United States Patent [19]

Hort

[11] 4,002,694
[45] Jan. 11, 1977

[54] ETHYNYLATION CATALYST AND PROCESS FOR PRODUCING ALKYNOLS

[75] Inventor: Eugene V. Hort, Wayne, N.J.

[73] Assignee: GAF Corporation, New York, N.Y.

[22] Filed: Aug. 11, 1975

[21] Appl. No.: 603,642

Related U.S. Application Data

[63] Continuation-in-part of Ser. No. 246,607, April 24, 1972, Pat. No. 3,900,759.

[52] U.S. Cl. .................. 260/635 Y; 252/431 R; 260/638 Y
[51] Int. Cl.² ............... C07C 29/00; C07C 33/04
[58] Field of Search ................ 260/635 Y, 638 Y

[56] References Cited

UNITED STATES PATENTS

| | | | |
|---|---|---|---|
| 2,238,471 | 4/1941 | Keyssner et al. | 260/635 Y |
| 2,871,273 | 1/1959 | Pehn | 260/635 Y |
| 3,433,581 | 3/1969 | Stephens et al. | 423/213.2 |
| 3,560,576 | 2/1971 | Kirchner | 260/635 Y |
| 3,723,545 | 3/1973 | Nagel et al. | 260/635 Y |

*Primary Examiner*—Joseph E. Evans
*Attorney, Agent, or Firm*—Walter C. Kehm

[57] ABSTRACT

Alkynols such as butynediol and propargyl alcohol are produced from acetylene and an aldehyde such as formaldehyde in the presence of a novel ethynylation catalyst comprising a copper acetylide complex on a transitional alumina carrier.

18 Claims, No Drawings

ETHYNYLATION CATALYST AND PROCESS FOR PRODUCING ALKYNOLS

REFERENCE TO RELATED APPLICATION

This application is a continuation-in-part of application U.S. Ser. No. 246,607, filed April 24, 1972 now U.S. Pat. No. 3,920,759.

BACKGROUND OF THE INVENTION

This invention relates to a process for producing alkynols by a low pressure ethynylation reaction from an aldehyde and an acetylene in the presence of a catalyst comprising a copper acetylide complex supported on a transitional alumina carrier.

Alkynols are prepared in accordance with the well known processes such as those described in U.S. Pat. Nos. 2,232,867; 2,300,969; 2,487,006–9; 2,712,560; 2,768,215; 3,108,104; 3,294,849; and 3,560,576, viz., by reacting aldehydes with an acetylenic hydrocarbon of the general formula $R-C \equiv C-H$, wherein R represents hydrogen or the radical of a hydrocarbon, such as methyl, vinyl, or phenyl. The acetylene or acetylenic hydrocarbon is introduced into the reaction zone as a gas, while the aldehyde can be a liquid under reaction conditions, or can be present in a liquid solvent or diluent. Typically, the reaction involves the reaction of acetylene and formaldehyde to yield butynediol and propargyl alcohol. It is known that the reaction proceeds at moderately elevated temperatures of from 50° to 150° C. at superatmospheric pressures, generally from 2 to 30 atmospheres. It has been stated to be desirable to conduct the reaction at a pressure less than 10 atmospheres and with careful temperature control to reduce the danger of explosion. Even at these pressures, the acetylene gas has been diluted with inert gases or vapors e.g., nitrogen, hydrogen or carbon dioxide in order to reduce the danger of explosion. However, even under these conditions, the danger of explosion still exists with the prior art processes.

The above-mentioned ethynylation reactions generally employ some form of cuprous acetylide complex catalyst, either supported or unsupported, which catalyst may be generated or made active by a variety of methods and from a variety of copper compounds. Often they are used together with a bismuth compound to minimize undesired cuprene formation, minimizing undesired acetylene polymerization. Supported catalysts used in the high pressure reaction systems are produced by impregnating the support with a solution of bismuth and copper salts such as the nitrates, drying and calcining to produce the metal oxides. The copper oxide thereafter is converted to an acetylide complex in situ by suitable treatment with acetylene and formaldehyde.

To achieve low ethynylation operating costs, it has been preferred to use the supported catalyst in pellet form in a fixed bed, plug flow process. Dilute aqueous formaldehyde and injection of acetylene at relatively high pressure are employed to convert excess formaldehyde and minimize distillation requirements to produce a product of requisite purity. However, this approach has necessitated high reactor costs to permit use, not only at normal acetylene operating pressures of up to 26 atmospheres, but also at the high pressures of up to 20 times greater than normal which occur coincidentally with the occasional acetylene decomposition which occurs at high pressures.

It has been proposed to employ such supported catalysts as slurries in continuous agitated reactions. Hitherto in such systems, however, not only has it been found necessary to remove and purify the catalyst at frequent intervals to avoid fouling, but even with continuous complete catalyst purification and recycle, it has been necessary also to operate at relatively low formaldehyde conversions and relatively high acetylene pressures to achieve even marginally acceptable space/time yields. Where such low pressure systems have been employed, the yield and purity of product have not been sufficient to warrant commercial use of such a system. Such processes have, heretofore, involved higher operating costs than fixed bed, plug flow processes because of the higher product separation expense and have offered little in the way of savings because of the relatively poor rate of reaction and inferior catalyst life.

In general, it has been found, that unsupported active acetylide catalysts prepared from cuprous compounds, or from cupric compounds in such a way that a substantial portion of the cupric compound is reduced to cuprous copper before formation of the acetylide, tend to have a low carbon to copper ratio in which condition, they have been described as being in the form of small, sticky, relatively explosive particles, commonly containing appreciable amounts of metallic copper. Furthermore, it has been claimed in the literature that generated cuprous acetylide complex catalysts prepared from cupric compounds under an acetylene partial pressure of greater than 2 atmospheres or in the absence of formaldehyde, or in the presence of radically unbalanced amounts of acetylene or formaldehyde, or from cupric compounds which are highly soluble or dispersed in media where the compounds tend to dissolve, tend to have an insufficient total surface area and are accordingly not very effective, vis-a-vis, production of the alkynol.

A catalyst based upon high surface copper carbonate or certain other insoluble copper compounds has been described (U.S. Pat. No. 3,560,576) as one which obviates the aforedescribed difficulties. It has been shown, however, that such a catalyst is very sensitive and permanently loses activity upon being starved for either formaldehyde or acetylene and, as pointed out therein, can easily be detonated by heating to 162° C.

In copending application Ser. No. 246,607, filed Apr. 24, 1972, and assigned to the assignee of this application, there is described a low pressure ethynylation catalyst comprising a water-insoluble cuprous acetylide complex catalyst supported on a magnesium silicate carrier. The catalyst disclosed therein provides substantial advantages over the cuprous acetylide complex ethynylation catalysts of the prior art such as those supported on carbon or silica including its retention of activity for long periods and its promotion of butynediol formation at an increased rate. Even though this catalyst provides substantial advantages over the other catalysts of the prior art, it has one disadvantage.

It has been found during use of the above cuprous acetylide complex — magnesium silicate catalyst, that most of the magnesia thereof is rapidly leached from the magnesium silicate support, followed by a continuing slow dissolution of silica therefrom such that, after the reaction has reached equilibrium, about 200 ppm of dissolved silica can be found in the reaction medium. The magnesia and silica contaminate the product and may cause difficulties in further processing. In addition, this leached catalyst is relatively weak and tends to break-up into fine particles under the normal mechanical forces encountered while conducting the reaction. This causes difficulties in separating the catalyst from the product thereby resulting in increased cost of separation or in product contamination.

It would be desirable to provide an ethynylation catalyst which is active and selective for the conversion of acetylene and an aldehyde to an alkynol and which is not readily explosive, nor difficult to remove from the product nor overly active in forming cuprene. Furthermore, it would be desirable to provide such a catalyst which can be formed in situ during the reaction and which promotes substantial reaction at lower and safer acetylene reaction pressures. In addition, it would be desirable to provide such a catalyst having good physical strength and which is not soluble in the reactants or reaction products so that it can be used for long periods without contaminating the product.

SUMMARY OF THE INVENTION

This invention provides (a) a particulate, water-insoluble ethynylation catalyst comprising a cuprous acetylide complex supported on a powdered transitional alumina carrier as well as (b) a catalyst precursor comprising a reducible copper oxide supported on a powdered transitional alumina carrier. For purposes of this invention, (a) the cuprous acetylide complex is as defined in U.S. Pat. No. 3,560,576, particularly as described in Column 3, lines 11–60, whose disclosure in this regard is hereby incorporated herein by reference; and (b) the transitional alumina carriers described herein may be defined as comprising nearly anhydrous aluminas having a $H_2O/Al_2O_3$ mole ratio of about 0.02 to about 0.5 and a surface area of at least about 10 $m^2/g$, preferably greater than 25 $m^2/g$, and most preferably about 100 to 500 $m^2/g$. Such transitional aluminas may be made from suitable sources thereof such as alumina hydrates: alumina monohydrates, alumina dihydrates, and alumina trihydrates; mixed alkali or alkaline earth metal oxides — aluminum oxides such as $Na_2O.11Al_2O_3$; $K_2O.11Al_2O_3$; $MgO.11Al_2O_3$; $SrO.6Al_2O_3$; $BaO.6Al_2O_3$; $Li_2O.5Al_2O_3$; etc. Since the nomenclature is such in the alumina art that there are many aluminas or hydrates thereof that are known by several different names of synonyms, the following classification of names and properties of aluminas — as contained in the Kaiser Aluminum & Chemical Corporation, Kaiser Chemicals Division publication on Specialty Aluminas, Section 1-5, effective 9-1-72, relating to General Information, Properties of Aluminas — is set forth.

| PROPERTIES OF ALUMINAS | | | | |
|---|---|---|---|---|
| Name and Synonyms | $H_2O/Al_2O_3$ (mol) | Crystal System | Space Group | Unit Axis Length, A |
| TRIHYDRATES: | | | | |
| Pseudoamorphous: Amorph. Trihydrate; Ca Gel (?) | ≃3.0 | ≃ Amorphous | | |
| Bayerite: β-Trihydrate (Am): α-Trihydrate (Ger) | 3.0 | Monoclinic | $C_{2h}^5$ | 8.674, 5.061, 4.713 90° 00' |
| Nordstrandite: γ-Trihydrate (Am); Randomite; Bayerite II; Bauxite Dihydrate | 3.0 | Monoclinic and Triclinic | | 8.63, 5.01, 19.12; 92° 00' |
| Gibbsite or Hydrargillite; α-Trihydrate (Am); γ-Trihydrate (Ger) | 3.0 | Monoclinic (Triclinic?) | $C_{2h}^5$ | 8.62, 5.06, 9.70; 85° 26' |
| DIHYDRATE: | | | | |
| Pseudoboehmite; gelatinous boehmite; boehmite | ≃1.5–2.0 | Orthorhombic | $D_{2h}^{17}$ | 2.87, 13.127, 3.70 |
| MONOHYDRATES: | | | | |
| Boehmite; α-monohydrate (Am); γ-monohydrate (Ger) | 1.0–1.15 | Orthorhombic | $D_{2h}^{17}$ | 2.868, 12.227, 3.700 |
| Diaspore; β-monohydrate (Am); α-monohydrate (Ger) | 1.0 | Orthorhombic | $D_{2h}^{16}$ | 4.396, 9.426, 2.844 |
| TRANSITION: | | | | |
| Rho-(Fr) | ≃ 0.5 | Amorphous | | |
| Chi-rho-(Kaiser) | ≃ 0.3 | Amorphous | | |
| Eta-(Am); gamma-(Br) | ≃0.12 | Cubic (spinel) | | 7.90 |
| Chi-(Am;Ger); (Fr(Thibon)) | ≃ 0.12 | Cubic (not spinel) | | 7.95 |
| Gamma-(Am); delta-(Br) | ≃ 0.12 | Cubic (deformed spinel) | | 7.96, 7.82 |
| Pseudogamma-(Kaiser) | ≃ 0.12 | Cubic (deformed) | | |
| Kappa-(Am;Ger); (Fr(Thibon)) | ≃ 0.12 | Orthorhombic | | 8.49, 12.73, 13.39 |
| Delta-(Am;Ger;Fr); | ≃ 0.07 | Orthorhombic | | 4.25, 12.75, 10.21 |
| Theta-(All) | ≃ 0.02 | Monoclinic | $C_{2h}^3$ | 5.63, 2.95, 11.86; 103° 42' |
| Iota-(Am) | ≃ 0.01 | Orthorhombic | | 7.73, 7.78, 2.91 |
| ANHYDROUS: | | | | |
| Alpha-(All) Corundum | ≃ 0.00 | Hexagonal | $D_{3h}^6$ | 4.758 12.991 |

| Name and Synonyms | $H_2O/Al_2O_3$ (mol) | Measured Density, g/cc | Surface Area $m^2/g$ | Number of Forms | MOLs/ Unit Cell | Remarks |
|---|---|---|---|---|---|---|
| TRIHYDRATES: | | | | | | |
| Pseudoamorphous Amorph. Trihydrate: Ca Gel(?) | 3.0 | | 20–100 | Probably several | 2 | Probably occurs with those hydrates having appreciable surface |
| Bayerite: β-Trihydrate (Am). α-Trihydrate (Ger) | 3.0 | 2.53 & 2.4 | 0–50 (Pseudo- amorphous?) | Probably 2 | 2 or 4 | Surface may be due to mixed pseudoamorphous |
| Nordstrandite: γ-Trihydrate (Am); Randomite:Bayerite II; Bauxite Dihydrate | 3.0 | 2.50 | 0–40 (Pseudo- amorphous?) | Probably 2 | 16 | Surface may be due to mixed psuedoamorphous; Mean Pore 28 A; in Nature |
| Gibbsite or Hydrargillite; α-Trihydrate (Am); γ-Trihydrate (Ger) | 3.0 | 2.42 | ≈ 0 | Perhaps 2 | 4 | Most common of trihydrates |
| DIHYDRATE: | | | | | | |
| Pseudoboehmite; gelatinous boehmite; boehmite | 1.5–2.0 | | 300–500 | Linear transition to boehmite | 2 | d(020) 6.5– 6.7 A. Some $H_2O$ structurally coordinated |
| MONOHYDRATES: | | | | | | |
| Boehmite; α-monohydrate (Am); γ-monohydrate (Ger) | 1.0–1.15 | 3.01 | 0–15 | 1 | 2 | d(020) 6.13– 6.15. $H_2O$ is structurally combined |
| Diaspore; β-monohydrate (Am); α-monohydrate (Ger) | 1.0 | 3.44 | ≈ 0 | 1 | 2 | Goes directly to α-$Al_2O_3$ on heating |
| TRANSITION: | | | | | | |
| Rho-(Fr) | 0.5 | | 50–200 | Probably several | | From vacuum dehydration |
| Chi-rho- (Kaiser) | 0.3 | | ≈ 350 | Probably several | | Some diffuse chi-lines |
| Eta-(Am); gamma-(Br) | 0.12 | 2.5–3.6 | 300–500 | 1 | 10 | Eta-(Fr); gamma-(Ger) |
| Chi-(Am;Ger); (Fr(Thibon)) | 0.12 | 3.0 | 300–400 | 1 | 10 | Chi- + gamma- (Br;Fr(Pechiney)) |
| Gamma-(Am); delta-(Br) | 0.12 | 3.2 | <100 | 1 | 8? | Gamma-(Ger;Fr) |
| Pseudogamma- (Kaiser) | 0.12 | | ≈ 500 | Several | 10? | |
| Kappa-(Am;(Ger); (Fr(Thibon)) | 0.12 | 3.1–3.3 | <75 | 1 | 32 | Kappa- + theta- (Br); kappa- + delta(Fr(Pechiney)) |
| Delta-(Am;Ger;Fr) | 0.07 | 3.2 | <50 | 2 | 12 | Delta- + theta-(Br) |
| Theta-(All) | 0.02 | 3.56 | <25 | 1 | 4 | |
| Iota-(Am) | 0.01 | 3.71 | <10 | 1 | 4 | Under special conditions only; rare |
| ANHYDROUS: | | | | | | |
| Alpha-(All) Corundum | 0.00 | 3.98 | ≈ 0 | 1 | 2 | Ruby; Sapphire |

NOTES: Under Unit Axis Lengths, values for a, b, and c axes, respectively, are given. Angle given when applicable. Surfaces are BET $N_2$ surfaces, and vary with preparation. In some instances the major part of the surface is probably due to essentially amorphous material, undetected by XRD. Underlined name is the preferred one in America.

The catalyst precursor can be prepared by impregnating an unstable form of a transitional alumina or a hydrated alumina with a copper salt and then roasting the thus — impregnated alumina to convert the copper salt to copper oxide and the unstable or hydrated alumina to a stable transitional alumina. The catalyst precursor also can be prepared by directly impregnating a stable form of a transitional alumina with a copper salt followed by roasting to convert the copper salt to copper oxide.

The catalyst and catalyst precursor also can contain 0 to about 5% by weight bismuth, preferably about 2% to about 3% by weight bismuth, which minimizes undesired cuprene formation without unacceptable effect on alkynol production. The active catalyst is formed by contacting a catalyst precursor in an aqueous formaldehyde medium at a temperature of about 70° C to about 120° C., with acetylene, preferably at an acetylene pressure of less than 2 atmospheres absolute pressure.

The active catalyst is useful in forming alkynols from acetylene and an aldehyde, particularly formaldehyde, to form butynediol and propargyl alcohol.

DESCRIPTION OF SPECIFIC EMBODIMENTS

This invention will be described hereinafter with reference to the reaction of formaldehyde and acetylene. However, it is to be understood that aldehyde reactants other than formaldehyde can be employed, e.g., other lower alkanols such as acetaldehyde, propionaldehyde, butyraldehyde or the like.

In a preferred embodiment of this invention, the catalyst precursors of this invention are prepared by first impregnating an unstable form of a transitional alumina or a hydrated alumina with a copper salt. The impregnated alumina then is roasted at a temperature and for a time sufficient to convert the copper salt to copper oxide and to convert the hydrated alumina or unstable transitional alumina to a stable transitional alumina. For purposes of this invention any unstable transitional alumina that is useful herein is one which can be converted to a stable transitional alumina during roasting from about 450° to 600° C. for about 1 to 12 hours. A stable transitional alumina is one which will not be converted to another alumina phase to a major extent under these conditions of time and temperature. Representative unstable transitional aluminas are chi-rho alumina and rho alumina, as defined above. Alternatively, the catalyst precursor can be prepared by directly impregnating a stable transitional alumina with a copper salt and then roasting the impregnated alumina to convert the copper salt to copper oxide. It has been found that active catalysts prepared from catalyst precursors formed from an unstable transitional alumina, particularly the chi-rho alumina, or a hydrated alumina often exhibit greater activity than catalyts prepared from catalyst precursors formed initially from stable transitional aluminas. It is preferred to form the catalyst precursor initially from the chi-rho alumina since the catalysts produced therefrom exhibit greater activity than many catalysts produced from catalyst precursors formed initially from hydrated aluminas or stable transitional aluminas. The alumina trihydrates, dihydrates or monohydrates per se, are unsuitable as the support for the activated catalysts due to their lack of structural stability in hot aqueous solutions and frequently inadequate surface area. The alpha phase alumina also is unsuitable for use in this invention since it has a low surface area. Typical hydrated aluminas suitable for forming the catalyst precursors of this invention include the trihydrates such as bayerite, gibbsite or nordstandite; the dihydrates such as pseudoboehmite or a monohydrate such as boehmite. The hydrated aluminas can be converted to the transitional aluminas by dehydration as described hereinabove. As noted above, the aluminas employed in this invention in forming the catalyst precursor and/or the active catalysts can contain varying water concentrations as follows:

| Form of Alumina | $H_2O : Al_2O_3$, mole ratio |
|---|---|
| Trihydrate | about 3.0 |
| Dihydrate | about 1.5 – 2.0 |
| Monohydrate | about 1.0 – 1.15 |
| Rho | about 0.5 |
| Chi-Rho | about 0.3 |
| Usable Stable Transitional Forms | about 0.02 – 0.12 |

The active catalyst of this invention comprises a water-insoluble powder comprising copper acetylide complex supported on a transitional-alumina carrier therefor. Such catalyst contains between about 5 and about 25% by weight copper, and preferably between about 10 and about 15% by weight copper, based upon the total weight thereof. The stable transitional alumina carrier (of the active catalysts or employed to form the catalyst precursor) may comprise partially dehydrated alumina powder including gamma-alumina, eta-alumina, pseudogamma-alumina, kappa-alumina, delta-alumina, and the like. The alumina employed herein as discussed has a surface area per unit volume of at least about 10 m²/gram, preferably greater than 25 m²/gram, in order to promote high conversion of the reactants to the desired product. The bulk density of the catalyst generally ranges from about 0.4 to about 1.5 grams/cc. The catalyst of this invention may contain bismuth in an amount of between 0 and about 5% by weight, preferably about 2% to about 3% by weight based upon the total weight of catalyst in order to minimize undesired cuprene formation.

The catalyst of this invention provides substantial advantages over the prior art cuprous acetylide complex catalysts employed to promote the reaction of acetylene with formaldehyde. The catalysts of this invention are at least as active as those of the prior art for the formation of alkynols. Unlike unsupported catalysts, such as those described in U.S. Pat. No. 3,560,576, they are not explosive even when subjected to severe shock and heat and thus are far safer than those of the prior art. In addition, the active catalyst of this invention can be prepared in situ during the formation of the alkynol at the preferred low acetylene partial pressures of about 2 atmospheres or less. Furthermore, the catalysts of this invention exhibit excellent stability including resistance to attrition and insolubility of the carrier in the reaction products or reactants encountered in the reaction system. Therefore, the catalysts of this invention have a substantially improved useful life and need not be replaced before they become deactivated. Furthermore, the catalysts of this invention can be separated easily from the product by physical means such as filtration or centrifugation and maintain this ease of separation. Also, catalysts of this invention do not become permanently deactivated when starved for either the formaldehyde or acetylene reactant. As a result of the improved characteristics of the catalysts of this invention, the alkynol product obtained from their use has little or no catalyst contamination either from the catalyst, per se, or from soluble constituents or derivatives of the catalysts and can be employed in a continuous or semi-continuous process wherein the relative concentration of formaldehyde and acetylene changes over the course of the reaction.

The particle size of the resultant catalyst, while not in general a factor that is critical to the successful practice of this invention, is preferably small in size, preferably ranging from a particle size of between about 1 micron and about 1 mm so that the catalyst has a high surface area and activity and can be separated easily from the liquid products. In general, particle sizes below 1 micron are not preferred because they are too small to be easily separated by conventional means, and particle sizes above about 1 mm tend to give slower reaction rates and be more difficult to pump and hence are likewise not preferred. Optionally, impregnation can be carried out with the addition of a bismuth salt to function as an inhibitor of acetylene polymerization activated by copper metal. The impregnated mixture is heated to drive off volatiles, convert any unstable aluminas to a stable transitional alumina, and to convert the salts to the cupric oxide precursor of the active catalyst. Generally, the desired conversion is carried out by heating the impregnated alumina at a temperature between about 450° and 600° C., for a period from about 1 to 12 hours. Repeated tests have shown that the generated cooper-impregnated transitional alumina powdered catalyst of the instant invention cannot be either detonated or burned, unlike unsupported copper-containing catalyts of the prior art. Furthermore, the transitional alumina is insoluble in the liquid reactants and products and is sufficiently strong as to withstand the mechanical forces normally encountered during the process.

The active catalyst is prepared by reduction of the cupric compound to the cuprous compound by subjecting the catalyst precursor, in an aqueous medium maintained at a temperature of about 70° to about 120° C., preferably to the simultaneous action of formaldehyde and acetylene at a partial pressure of less than 2 atmospheres thereby generating the active catalyst. Active catalyst generation and alkynol synthesis can go forward continuously and simultaneously with the catalyst as a slurry in an aqueous medium in a continuous stirred reactor at said temperature. As an alternative, however, one can first generate the catalyst in a separate reaction zone and then place it in the ethynylation reaction zone where the latter reaction can then be carried out. As a further alternative to either of the aforesaid processes, the generated catalyst can be employed (either manner of generation having been followed) until the activity thereof drops below a desired point; at which time, the catalyst can then be replaced with fresh catalyst either by completely removing the former or by withdrawing portions thereof while at the same time adding fresh catalyst to the reaction medium.

In any case, in the generation procedure, the stable transitional alumina impregnated with copper salt is reduced. The reduction of the cupric compound and the subsequent production of alkynol therewith can be carried out in the same reactor, thereby forcing both the generation of catalyst and alkynol product to be continuous and simultaneous at all times. The cupric precursor is subjected in situ to the simultaneous action of the reactants at the required pressure in a substantially aqueous medium at the temperature of about 60° to 120° C., preferably from 80° to 100° C. At temperatures substantially outside this range, or in strongly basic or acidic media, or at low formaldehyde concentrations, or with an adequate supply of acetylene, poor catalyst tends to result. The pH of the aqueous medium is in the range of 3 to 10 and preferably 4 to 7. The concentration of formaldehyde in the aqueous medium is preferably at least 6% by weight. The acetylene partial pressure is in the range of 0.1 to 1.9 atmospheres; preferably it is in the range of 0.4 to 1.5.

In carrying out the catalyst generation, nitrogen or another substantially inert gas such as methane or carbon dioxide can be present, as can also the common components of crude acetylene, such as ethylene. Oxygen is preferably excluded for safety reasons. The supported cupric precursor can be slurred in cold neutral formaldehyde solution and the acetylene introduced before the slurry is heated. The aqueous solution can advantageously be a stream containing propargyl alcohol and/or butynediol, e.g., a recycle stream.

The catalyst generation reaction is preferably continued until the cupric copper is substantially completely converted to the cuprous acetylide complex, which with the preferred cupric precursors, generally requires 1 to 24 hours after all the precursor has been contacted under the prescribed conditions. Preferably, also, the prescribed conditions of temperature, pH and acetylene and formaldehyde concentrations will be maintained throughout the catalyst generation. Activated catalyst also can be prepared by incremental addition of make-up catalyst precursor during a continuous process. However, departures from the prescribed conditions during the course of the preparation reaction can be tolerated, as the reaction is relatively insensitive to minor changes in operating conditions.

The pH of the aqueous medium normally decreases as the reaction proceeds, at a rate and to an extent which tends to increase with the initial formaldehyde concentration, with the initial acidity of the reaction medium and with the reaction temperature. Accordingly, the pH can be, and advantageously is, controlled to some extent by beginning at the preferred initial pH of 4 to 7, to some extent by operating in the preferred temperature range of 60° to 120° C. Additional control can be achieved by adding small amounts of acid acceptor such as sodium acetate as the reaction proceeds. Further control can be achieved by carrying out the catalyst generation as a continuous stirred reaction, while fresh neutral formaldehyde solution is continuously introduced into an agitated reaction zone as the reaction proceeds, and while maintaining the acetylene partial pressure. During this step, any acidic effluent, if desired can be filtered away from the copper-containing particles.

The ethynylation reaction per se, comprises contacting the reactants at an acetylene partial pressure of not more than about 2 atmospheres with an aqueous formaldehyde slurry of the catalyst as above-described, in a continuously stirred reaction at 80° to 120° C. The formaldehyde and acetylene are preferably continuously fed into the reaction zone where they are introduced into and preferably below the surface of, the aqueous catalyst slurry, and thoroughly mixed into the same by vigorous agitation, and effluent is continuously withdrawn.

The reaction temperature for ethynylation is desirably about 60° to about 120° C., advantageously 80° to 115° C. and preferably 85° to 105° C. Advantageously, the pH of the reaction mixture will be in the 3 to 8 and preferably 4 to 7 range, and can be maintained by ion exchange or acid acceptor treatment of the continuous feed or by addition of a suitable buffering agent.

The formaldehyde concentration in the liquid medium in contact with the slurried catalyst in the course of the ethynylation reaction will be ordinarily 0.5 to 50% by weight, under steady state conditions. Advantgeously, the acetylene partial pressure will be in the range of 0.4 to 1.9 atmospheres. Preferably, the acetylene partial pressure above the aqueous medium will be 0.5 to 1.5 atmospheres and the catalyst will be present in amounts of about 1 to 25 weight parts per 100 weight parts of aqueous medium. For the purpose of the present invention, in the substantial absence of extraneous gas, the acetylene partial pressure can be taken as the total pressure minus the absolute pressure of water and methanol, formaldehyde, and propargyl alcohol, at the reaction temperature. As in the catalyst generation, crude acetylene can be used, but for safety reasons, it should be advantageously substantially free of oxygen.

The effluent from the reaction zone can be heated in a still to volatilize formaldehyde, propargyl alcohol and a portion of the water which are condensed and combined with supplemental concentrated formaldehyde for recycle to the ethynylation reactor, purging any buildup of methanol at convenient intervals in a continuous operation, and sending the balance of effluent as aqueous butynediol directly to subsequent treatment such as hydrogenation. Alternatively, effluent from the reaction zone can be fed to a conventional plug flow ethynylation zone to react any excess formaldehyde.

In a particular embodiment of this invention, the reaction can be carried out in a multi-stage reaction system wherein a mixture of the catalyst, formaldehyde and acetylene are introduced into a first stage at a relatively high formaldehyde concentration e.g. 30% – 37% by weight, and thereafter passed, in admixture, to a plurality of downstream reactors in sequence to obtain increased conversion of the formaldehyde. The reaction mixture is removed from the last reactor and directed to a gas-liquid separator wherein unreacted acetylene is separated from the liquid reactants and products and the solid catalyst. The catalyst then is separated from the reaction products and unconverted formaldehyde by filtration, centrifugation or the like. The liquid obtained after catalyst separation then may be distilled to separate unconverted formaldehyde from the alkynol product and to separate the butynediol product from the propargyl alcohol. The separated catalyst and formaldehyde then are recycled to the first reaction stage. Make-up catalyst precursor may be added to the first stage wherein the highest formaldehyde concentration is maintained.

The invention will be more specifically described and explained by means of the following examples, which are not to be considered at limiting but merely illustrative of the invention. All parts and percentages therein as well as in the appended claims are by weight unless otherwise specified.

EXAMPLE 1

This example illustrates the improved stability of the catalyst of this invention against leaching by the reactants employed or products obtained by the process of this invention.

Three catalysts were prepared by mixing 100 g. of a catalyst support comprising respectively, kieselguhr, magnesium silicate or chi-rho alumina with 100 ml. of the following impregnation solution.
 702 g.: $Cu(NO_3)_2 \cdot 3H_2O$
 102 g.: $Bi(NO_3)_3 \cdot 5H_2O$
 60 g.: Conc. $HNO_3$
The impregnation solution was diluted to 1200 ml. total with water.

The impregnated supports were dried at 120° – 140° C. and then roasted by slowly heating at a rate of about 50° C. per hour and then maintaining the roasting temperature at about 480° C. for six hours to form a catalyst precursor comprising copper and bismuth oxides impregnated on the support.

The catalysts were activated and used to react formaldehyde and acetylene to form butynediol and propargyl alcohol. Catalyst activation was carried out by stirring 100 g. of the catalyst with 1 liter of a 35% aqueous solution of formaldehyde at 80° C. under an acetylene pressure of one atmosphere. Activation was completed in 4 hours with the kieselguhr and alumina and in 24 hours with the magnesium silicate during which period, the catalysts became activated and conversion to butynediol and propargyl alcohol was effected. After activation, the catalysts were each used to ethynylate one liter of 10% aqueous formaldehyde solution with acetylene at one atmosphere pressure at 80° C. for a period of 24 hours.

Upon completion of this reaction period, the catalysts were each separated by filtration from the liquid reaction medium comprising butynediol, propargyl alcohol and formaldehyde. The recovered liquid reaction medium then was analyzed to determine the amount of catalyst support solubilized in the liquid reaction medium. The results are shown in Table I.

Table 1

| Catalyst Support | Concentration in Liquid Reaction Medium, ppm |
|---|---|
| A) Kieselguhr | 100 ($SiO_2$) |
| B) Magnesium Silicate | 200 ($SiO_2$) + some magnesia |
| C) Chi-Rho Alumina | 1 ($Al_2O_3$) |

The initial unimpregnated chi-rho alumina (Kaiser KA-300) had a surface area of 350 $m^2$/gram. On roasting, it was converted to a mixture of eta and pseudo-gamma phase aluminas. As shown in Table I, this alumina support for the catalyst of this invention is far less soluble in the liquid reaction medium than are the kieselguhr or magnesium silicate supports. Furthermore, it was found that the alumina supported catalyst converted formaldehyde and acetylene to butynediol at a rate similar to that obtained with the other two catalysts but give a ratio of propargyl alcohol to butynediol three times that obtained with the magnesium silicate supported catalyst or kieselguhr supported catalyst.

EXAMPLE II

The active catalyst prepared from the chi-rho alumina by the procedure of Example 1 was used to catalyze the reaction of acetylene and formaldehyde.

Ten grams of the active catalyst was stirred with 500 ml. of a 10% aqueous formaldehyde solution at 80° C. for 50 hours. Thereafter, the filtrate comprised 1.8% formaldehyde, 10.9% butynediol and 0.6% propargyl alcohol.

EXAMPLE III

This example illustrates a method for preparing the catalyst precursor of this invention, activating the catalyst precursor and utilizing the activated catalyst. A catalyst impregnating solution was prepared by mixing:
 880 g.: $Cu(NO_3)_2 \cdot 3H_2O$
 152 g.: $Bi(NO_3)_3 \cdot 5H_2O$
 75 g.: Conc. $HNO_3$
 Sufficient $H_2O$ to bring to 825 ml total volume.

After heating on a steam bath to complete solution, this solution was milled to homogeneity with 1650 g. gamma alumina (Norton Company LA-6373) having a surface area of about 250 $m^2$/gram. The impregnated alumina was separated by filtration and then roasted under an air stream at 480° C. for about 6 hours. The product was a dark green powder, had a surface area of 196 $m^2$/gram, and assayed 12.5% copper and 3.2% bismuth.

Ten grams of the catalyst precursor thus obtained was stirred with 500 ml. of a 35% aqueous solution of formaldehyde at 80° C. under an acetylene pressure of one atmosphere for 6 hours. The mixture was cooled, the liquid withdrawn through a filter stick and the catalyst sump used for a series of ethynylations.

Ethynylation was carried out by mixing 10 grams of the catalyst with 500 ml of a 10% aqueous formaldehyde solution, while stirring, under an acetylene atmosphere at one atmosphere pressure and heating the reactants, at 80° C. for 50 hours. Thereafter, the catalyst was separated by filtration and the remaining liquid was analyzed and found to comprise 9.6% butynediol, 0.5% propargyl alcohol and 2.8% formaldehyde.

EXAMPLE IV

An activated copper acetylide catalyst, without bismuth, was prepared by mixing:
 880 g.: $Cu(NO_3)_2 \cdot 3H_2O$
 75 g.: Conc. $HNO_3$
 300 ml.: $H_2O$ After heating on a steam bath to effect complete solution, this solution was milled to homogeneity with 1650 g. chi-rho alumina (Kaiser KA-300) having a surface area of about 350 $m^2$/gram and then roasted at about 480° to 500° C. for six hours. The product was a dark green powder and assayed 13.0% copper.

Ten grams of the catalyst precursor obtained was stirred with 500 ml. of a 33% aqueous solution of formaldehyde at 80° C. under an acetylene atmosphere at atmospheric pressure for 6 hours. The mixture was cooled and filtered to separate the activated catalyst from the liquid.

The separated catalyst was used to promote the reaction of formaldehyde and acetylene to butynediol and propargyl alcohol. Ten grams of the catalyst was mixed with 500 ml. of a 10% aqueous solution of formaldehyde and stirred under acetylene at atmospheric pressure and was heated at 80° C. for 50 hours. The catalyst and liquid then were separated by filtration. The recovered liquid product comprised 11.8% butynediol, and 0.7% propargyl alcohol and 1.1% formaldehyde.

EXAMPLE V

This example illustrates that copper acetylide catalysts supported on stable transitional aluminas can be prepared when employing a hydrated alumina starting material.

To 100 grams of each of the hydrated alumina supports set forth in Table II was added a solution comprising:

53 g.: $Cu(NO_3)_2 \cdot 3H_2O$
9 g.: $Bi(NO_3)_3 \cdot 5H_2O$
4.5 g.: Conc. $HNO_3$
100 ml.: $H_2O$ After heating on a steam bath to effect complete solution, the resultant pastes were milled to homogeneity. The trihydrate pastes were then dried at 120° for 12 hours and then the temperature raised at about 50° per hour to 480° C. and roasted at 480° C. in an air stream for 6 hours. The monohydrated alumina was treated similarly except that it was roasted at a higher temperature (550° C.). The roasted aluminas were converted to transitional aluminas as shown in Table II.

Table II

| Catalyst | Hydrated Alumina | Transitional Alumina | CuO, wt. % |
|---|---|---|---|
| 1 | α-Alumina Trihydrate | chi | 11.7 |
| 2 | β-Alumina Trihydrate | eta | 12.1 |
| 3 | α-Alumina Monohydrate | gamma | 11.0 |

Each of the roasted, copper-containing catalysts was activated by mixing 10 grams of the catalyst with 500 ml of a 35% aqueous solution of formaldehyde stirred under acetylene at atmospheric pressure at a temperature of 80° C. for 6 hours. The activated catalysts were recovered by filtration. The activity of the catalysts were determined by running with 10% aqueous formaldehyde for 50 hours at 80° C. and atmospheric pressure of acetylene. After reaction, the catalyst conversions were as follows:

| Catalyst | Residual Formaldehyde % |
|---|---|
| 1 | 3.5 |
| 2 | 3.7 |
| 3 | 2.0 |

EXAMPLE VI

This example shows that the catalyst of this invention does not permanently lose its activity in a reaction system containing a low concentration of formaldehyde.

Ten grams of the activated catalyst of Example 1C was stirred with 500 ml. of a 20% aqueous solution of formaldehyde under an acetylene pressure of one atmosphere at 90° C. for 6 hours. The catalyst was separated from the liquid reaction system by filtration. The reaction proceeded at a rate of 15 ml. of acetylene consumed per minute. Thereafter, the catalyst was exposed to a low concentration of formaldehyde by being mixed with 500 ml. of a 2% aqueous solution of formaldehyde under an acetylene pressure of one atmosphere at 90° C. for 6 hours, giving a rate of 3 ml of acetylene consumed per minute. When this catalyst was re-admixed with 500 ml. of a 20% aqueous solution of formaldehyde under an acetylene pressure of one atmosphere at 90° C., the initial rate of reaction was only 9 ml. of acetylene per minute for 6 hours. Upon once more repeating the reaction with 20% formaldehyde under the same conditions, the original rate of 15 ml. of acetylene per minute was restored.

Thus, the catalyst of this invention recovered its original activity and selectivity, as evidenced by the rates obtained even after having been starved for formaldehyde under normal reaction conditions. This example establishes that the catalysts of this invention can be employed in a continuous process for converting acetylene and formaldehyde to butynediol and propargyl alcohol even when starved for formaldehyde during the process since the activity of the catalyst is shown to be restored when subjected to normal reactant concentrations subsequent to formaldehyde starvation.

EXAMPLE VII

This example illustrates the use of this invention in a continuous process.

A stainless steel stirred autoclave of one gallon working capacity was charged with 500 grams of the catalyst of Example IV and 35 liters of 28% formaldehyde solution. The reactor was purged with acetylene and over a period of two hours the temperature was raised to 100° C. while the pressure was raised to 12 psig, continually passing fresh acetylene through the slurry.

When the operating conditions of 100° C. and 12 psig were reached, a steady addition of 0.7 liters of 28% formaldehyde per hour was initiated with the level in the reactor being maintained by withdrawing product steadily through an internal cartridge filter. After 20 hours the analyses of the effluent solution stabilized and remained nearly constant. The product contained 23.2% butynediol, 1.8%% propargyl alcohol, and 8.3% residual formaldehyde.

What is claimed is:

1. In a process for preparing an acetylenic alcohol by reacting a lower alkanol with acetylene at about 60° C to about 120° C., the improvement which comprises effecting reaction with acetylene at less than about 2 atmospheres partial pressure of acetylene in the presence of an ethynylation catalyst comprising a water-soluble cuprous acetylide complex and a stable transitional alumina powder carrier therefor having a $H_2O/Al_2O_3$ mole ratio of about 0.02 to about 0.5 and a surface area of at least about 10 m²/g, said cuprous acetylide complex being present in a concentration sufficient to catalyze the reaction of said aldehyde and said acetylene to said acetylenic alcohol.

2. In a process for preparing butynediol and propargyl alcohol by reacting formaldehyde with acetylene at about 60° C to about 120° C., the improvement which comprises effecting reaction with acetylene at less than about 2 atmospheres partial pressure of acetylene in the presence of an ethynylation catalyst comprising a water-soluble cuprous acetylide complex and a stable transitional alumina powder carrier therefor having a $H_2O/Al_2O_3$ mole ratio of about 0.02 to about 0.5 and a surface area of at least about 10 m²/g, said cuprous acetylide complex being present in a concentration sufficient to catalyze the reaction of said formaldehyde with said acetylene to said butynediol and propargyl alcohol.

3. In a process for preparing butynediol and propargyl alcohol according to claim 2 wherein said catalyst contains between about 5 and about 25 weight % copper.

4. In a process for preparing butynediol and propargyl alcohol according to claim 2 wherein said catalyst further comprises a bismuth compound in a concentration sufficient to suppress acetylene polymerization without unacceptably reducing the rate of said ethynylation reaction.

5. A process for producing butynediol and propargyl alcohol, comprising reacting formaldehyde and acetylene at a temperature of about 60° to about 120° C. and at less than about 2 atmospheres partial pressure of acetylene in an aqueous medium, in the presence of a particulate ethynylation catalyst comprising a water-insoluble cuprous acetylide complex containing about 5 to about 25% by weight, of copper supported on a powdered, stable transitional alumina carrier therefor having a $H_2O/Al_2O_3$ mole ratio of about 0.02 to about 0.5 and a surface area of at least about 10 $m^2/g$.

6. A process according to claim 5 wherein said reaction is carried out continuously.

7. A process according to claim 5 wherein said water-insoluble cuprous acetylide complex catalyst contains up to about 3% bismuth.

8. A low pressure process for the preparation of butynediol which comprises continuously reacting, in an aqueous medium, formaldehyde and acetylene at a temperature of about 60° C to about 120° C. and a pressure of about 0.4 to about 2 atmospheres partial pressure of acetylene in the presence of a particulate ethynylation catalyst comprising a water-insoluble cuprous acetylide complex containing, by weight of said catalyst, about 5 to about 25% copper, 0 to about 3% bismuth, supported on a powdered, stable transitional alumina carrier therefor having a $H_2O/Al_2O_3$ mole ratio of about 0.02 to about 0.5 and a surface area of at least about 10 $m^2/g$, said cuprous acetylide complex catalyst having been generated in said aqueous medium in the presence of formaldehyde and acetylene at a pressure of less than about 2 atmospheres partial pressure of acetylene and a temperature of about 60° to 120° C., from a copper oxide-containing precursor having, by weight of said precursor, about 5 to about 25% copper and 0 to about 3% bismuth.

9. A process according to claim 8 wherein the formaldehyde concentration in the aqueous medium is about 0.5 to about 60 weight %.

10. A process according to claim 8 wherein said aqueous medium is at a pH of about 3 to about 10.

11. A process according to claim 8 wherein said catalyst is present in amounts of about 1 to about 25 weight parts per 100 weight parts of aqueous medium during said reaction.

12. A process according to claim 8 wherein said copper oxide-containing precursor contains about 2% to about 3% bismuth.

13. In a process for preparing butynediol and propargyl alcohol according to claim 4, wherein said bismuth compound is bismuth at a concentration up to about 5 weight % of said catalyst.

14. A process according to claim 8 wherein said formaldehyde and acetylene are reacted in a plurality of stages.

15. A process according to claim 1 wherein the surface area of said catalyst is about 100 to about 500 $m^2/g$.

16. A process according to claim 2 wherein the surface area of said catalyst is about 100 to about 500 $m^2/g$.

17. A process according to claim 5 wherein the surface area of said catalyst is about 100 to about 500 $m^2/g$.

18. A process according to claim 8 wherein the surface area of said catalyst is about 100 to about 500 $m^2/g$.

* * * * *